(12) United States Patent
Walker

(10) Patent No.: US 6,337,454 B1
(45) Date of Patent: Jan. 8, 2002

(54) METHOD AND APPARATUS FOR DESTROYING A MEDICAL INSTRUMENT

(75) Inventor: Robert M. Walker, St. Catharines (CA)

(73) Assignee: Jack Warmbold, St. Catharines (CA)

( * ) Notice: Subject to any disclaimer, the term of this patent is extended or adjusted under 35 U.S.C. 154(b) by 0 days.

(21) Appl. No.: 09/101,390

(22) PCT Filed: Jan. 15, 1997

(86) PCT No.: PCT/CA97/00021

§ 371 Date: Jul. 15, 1998

§ 102(e) Date: Jul. 15, 1998

(87) PCT Pub. No.: WO97/26035

PCT Pub. Date: Jul. 24, 1997

(30) Foreign Application Priority Data

Jan. 16, 1996 (CA) ............................................. 2167332

(51) Int. Cl.[7] ......................... B23K 11/22; A61G 12/00; A61L 11/00
(52) U.S. Cl. ......................................................... 219/68
(58) Field of Search ............................................ 219/68

(56) References Cited

U.S. PATENT DOCUMENTS

| | | |
|---|---|---|
| 4,628,169 A | 12/1986 | Ch'ing-Lung ................ 219/68 |
| 4,639,567 A | 1/1987 | Stenzel |
| 4,877,934 A | 10/1989 | Spinello |
| 4,961,541 A | 10/1990 | Hashimoto |
| 4,965,426 A | 10/1990 | Colombo |
| 5,075,529 A | 12/1991 | Kudo |
| 5,091,621 A | 2/1992 | Butler |
| 5,138,125 A | 8/1992 | Salesses |
| 5,166,488 A | 11/1992 | Peppard |
| 5,264,675 A | 11/1993 | Butler |
| 5,276,297 A | 1/1994 | Nara |
| 5,282,428 A | 2/1994 | Greville et al. |
| 5,288,964 A | 2/1994 | Walker et al. |
| 5,294,767 A | 3/1994 | Cantarero |
| 5,300,752 A | 4/1994 | Elmerick et al. |
| 5,334,812 A | 8/1994 | Hsieh |
| 5,336,862 A | 8/1994 | Yelvington |
| 5,365,029 A | 11/1994 | Makihara |
| 5,391,849 A | 2/1995 | Furuya et al. |
| 5,468,928 A | 11/1995 | Yelvington |
| 5,525,772 A | 6/1996 | Tanguy |
| 5,540,416 A | 7/1996 | Huang |
| 5,548,095 A * | 8/1996 | Cornell ........................ 219/68 |

FOREIGN PATENT DOCUMENTS

| | | |
|---|---|---|
| CA | 2167332 | 7/1997 |
| EP | 0476823 A1 | 3/1992 |

OTHER PUBLICATIONS

B & A Enterprises Catalog For Needle Destroyer, No Publication Date.
Freisauer, Caroline, Needle–Ease Takes Sting Out Of Syringe Disposal, The Expositor; Mar. 28, 1996, p. 9, No. Publication Date.
Millenium Medical Supply Inc. Cat Alog, Needle–Ease Syringe Destroyer No. Publication Date.

* cited by examiner

Primary Examiner—Geoffrey S. Evans
(74) Attorney, Agent, or Firm—D. Peter Hochberg; Katherine R. Vieyra; William H. Holt

(57) ABSTRACT

A method and apparatus for destroying the metallic portion of an elongate medical instrument, such as a hypodermic needle, by locating the instrument in the apparatus in a position where the tip of the instrument electrically engages a contact surface of a first and a second electrode. The electrodes each have an electrical contact surface disposed in opposition and separated by a gap from each other, and each electrode is in electrical contact with a power source. The electric potential between the electrodes is sufficient to induce electrical resistance burning of the tip of the instrument when an electrical current is passed through the tip between the electrodes. During operation of the apparatus, the instrument is progressively advanced longitudinally relative to the electrodes to progressively consumes the shaft of the medical instrument as the burning tip continuously advances from the start position to a finish position.

20 Claims, 4 Drawing Sheets

METHOD AND APPARATUS FOR DESTROYING A MEDICAL INSTRUMENT

TECHNICAL FIELD

The invention is directed to an apparatus and method for destroying the metallic portion of an elongate medical instrument, such as a hypodermic needle or scalpel for example.

BACKGROUND OF THE ART

Conventionally, medical instruments such as hypodermic needles, syringes, scalpels, sutures and other metallic cutting means require careful disposal by inserting the instrument into an authorised container. These containers are designed to ensure that the disposal of the instrument does not cause any accidental cuts or punctures to caregivers or others involved in handling the waste.

The risk of accidental exposure to common bacteria, viruses and contraction of communicable diseases has always been a well known fact in such occupations. However recently, as a result of the extremely grave consequences of H.I.V. infection, the need to prevent accidental exposure has become literally a matter of life and death.

Questionable disposal practices have resulted in infected syringes washing up on populated beaches and as a result not only the medical profession but also the general public are painfully aware of the risks involved in improper or careless disposal.

The proper disposal of used medical instruments is a very serious task which requires attention to detail to ensure that risk of infection during disposal does not occur. However as long as the instrument remains capable of puncturing or cutting the skin, there remains a high risk of exposure to infection. Most prior art disposal focuses on the provision of superior containers which seal in the contents.

A different approach has also been taken wherein the cutting or puncturing capacity of the instrument is eliminated, thereby reducing the risk to that of common contaminated medical waste. The sharp metallic portions being removed or dulled reduces the risk of accidental infection substantially One example of such a device is described in U.S. Pat. No. 5,288,964 wherein high voltage is passed through the entire length of an elongate metal instrument to melt the metal portions. The electrical resistance of passing a current through stainless steel instruments is high which results in heat to melt the metal. However the electrical power demands of such a device are so high as to prevent common acceptance.

Considerable advantages exist however for such an approach. The high heat eliminates many bacterial and viral infection risks, and the destruction of sharp metallic portions minimises the risk of accidental skin puncture or cutting.

It is desirable therefore to produce a device which destroys or disarms the sharp portions of such instruments, preferably with high heat to disinfect if possible, while minimising electrical power consumption. By reducing the electrical demands of a device to generally available primary 110 volt power, the lower cost and portability increase the probability of commercial acceptance.

DISCLOSURE OF THE INVENTION

In accordance with the invention is provided a device and method which overcomes the aforementioned disadvantages in a novel manner. The invention provides an improved method and device for destroying metallic portions of elongate medical instruments, with reduced electrical power demands relative to the prior art.

Briefly, while the prior art requires the entire metal portion to be subjected to electrical current, the invention passes current through a narrow band of the metallic instrument. As the electrical resistance in such a narrow band heats up the band to melting or burning, the instrument is progressively advanced thereby consuming the metallic instrument in a progressive fashion rather than as a whole.

The electrical power consumption of experimental devices has been relatively low enabling hypodermic needles of 14 to 28 gauge to be destroyed using power supplies ranging from 3.15 Volts to 12 Volts. These voltages can be supplied by wet cell storage batteries dry cell battery packs, alkaline batteries, nickel-cadmium batteries or appropriate transformers with 110 volt input. Tests confirm that temperatures in the range of 2800 to 3000 degrees Fahrenheit (1500 to 1650 degrees Celsius) are generated in the exposed metal shaft of the stainless steel portion of such needles. These temperatures, by heat conduction, heat the encapsulated needle portion to temperatures of 1400 to 1600 degrees Fahrenheit (750 to 875 degrees Celsius) disinfecting these areas thereby remaining.

Residual metallic debris resulting from the process is minimal. For example, in one test it was estimated that the debris resulting from disposal of 10 needles is merely 0.3 grams. Of course the remaining non metallic portions of syringes etc. are disposed of in the conventional manner. However any risk of accidental puncture and degree of infectious contamination is substantially reduced as a result.

Specifically, the invention provides a method of destroying a metallic portion of an elongate medical instrument having a longitudinal axis, a tip and shaft, the method comprising the steps of: locating the instrument in a position wherein the tip of the instrument electrically engages a contact surface of a first and second electrode, each electrode having said electrical contact surface disposed in opposition and separated by a gap, and each electrode in electrical contact with power source means for creating an electrical potential difference between the electrodes, the potential difference being sufficient to induce electrical resistance burning of the tip of the instrument when an electrical current is passed through the tip between the electrodes; and progressively advancing the instrument and the electrodes longitudinally relative to each other, whereby the burning of the tip of the instrument progressively consumes the shaft as the burning tip advances from the start position to a finish position continuously in electrical contact with each electrode.

Also in accordance with the invention is provided a device for destroying a metallic portion of an elongate medical instrument having a longitudinal axis, a tip and shaft, the device comprising: a housing; first and second electrodes in the housing, each electrode having an electrical contact surface disposed in opposition and separated by a gap; means for moving the instrument to a start position wherein the tip of the instrument electrically engages the contact surface of each electrode; power source means for creating an electrical potential difference between the electrodes, the potential difference being sufficient to induce electrical resistance burning of the tip of the instrument when an electrical current is passed through the tip between the electrodes; and advancing means for progressively advancing the instrument and the electrodes longitudinally relative to each other, whereby the burning of the tip of the instrument progressively consumes the shaft as the burning tip advances from the start position to a finish position continuously in electrical contact with each electrode.

BRIEF DESCRIPTION OF THE DRAWINGS

In order that the invention may be readily understood, preferred embodiments of the invention and variations thereof will be described by way of example, with reference to the accompanying drawings wherein.

DETAILED DESCRIPTION OF PREFERRED EMBODIMENTS

Figure 1:
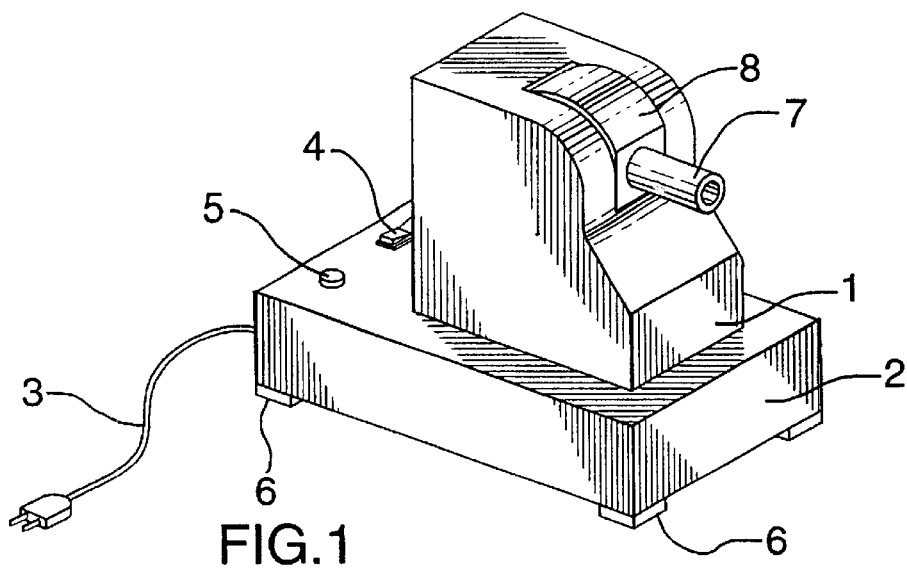
FIG. 1 is a perspective view of the outer appearance of a first embodiment of a device for destroying medical instruments, as illustrated using the example of hypodermic syringe.
Figure 2:
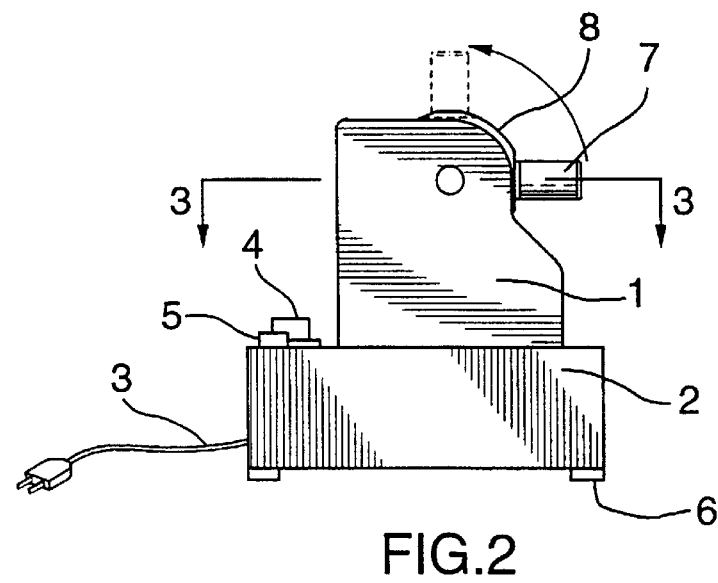
FIG. 2 is a side elevation view of the device of FIG. 1 showing the movement of the mandrel which positions and then advances the hypodermic syringe during destruction.

With reference to FIG. 1, the first preferred embodiment of the invention includes a housing 1 mounted on an electrical control box 2.

The control box 2 provides an electrical power source to the device in a conventional fashion, via standard electrical cord 3 when 110 volt power is used, and includes a power switch 4, fuse 5 and non-slip rubber feet 6. Due to the relatively low electrical power consumption of the device, the electrical power source as shown includes a transformer to convert 110 volt intake to 3.15 to 12 volt output. Other power sources may include 12 volt DC batteries, backup batteries, such as: wet cells; dry cells; alkaline; or nickel-cadmium batteries, mobile power sources, or generators.

Figure 3:
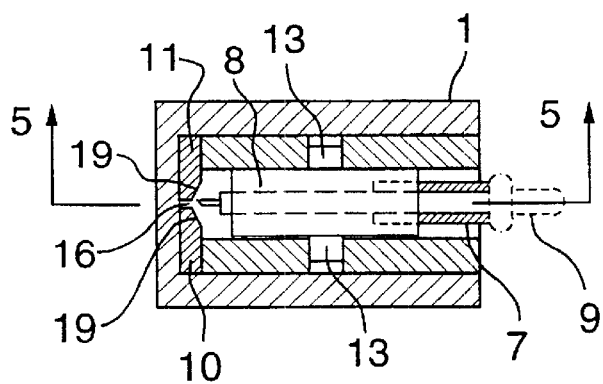
FIG. 3 is a sectional plan view along line 3—3 of FIG. 2, showing the syringe in dashed outline to the right as drawn, the electrodes housed to the left, and in the central area, an instrument holder which is journalled for rotation in the housing about a transverse axis.
Figure 4:
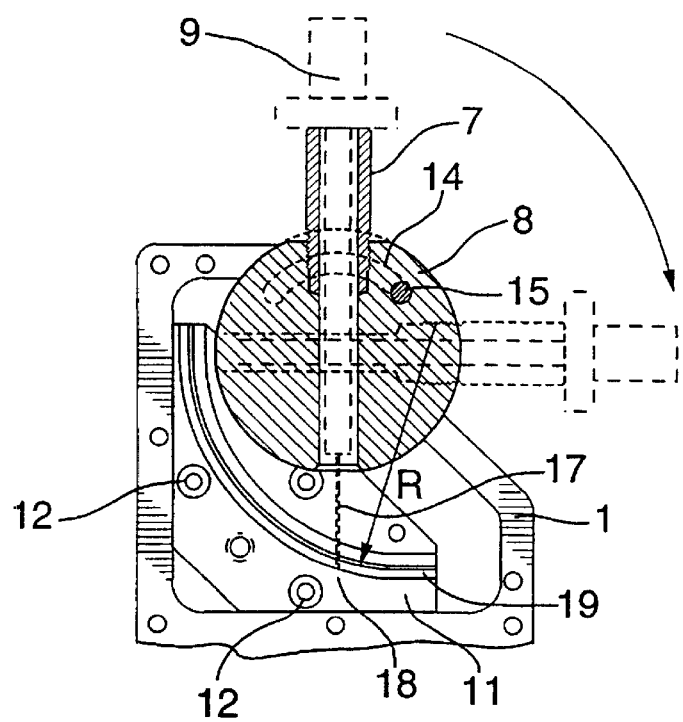
FIG. 4 is a sectional elevation view along line 5—5 of FIG. 3, with the holder in an upper start position, wherein the extreme original tip of the needle is initially contacted with the electrodes.
Figure 5:
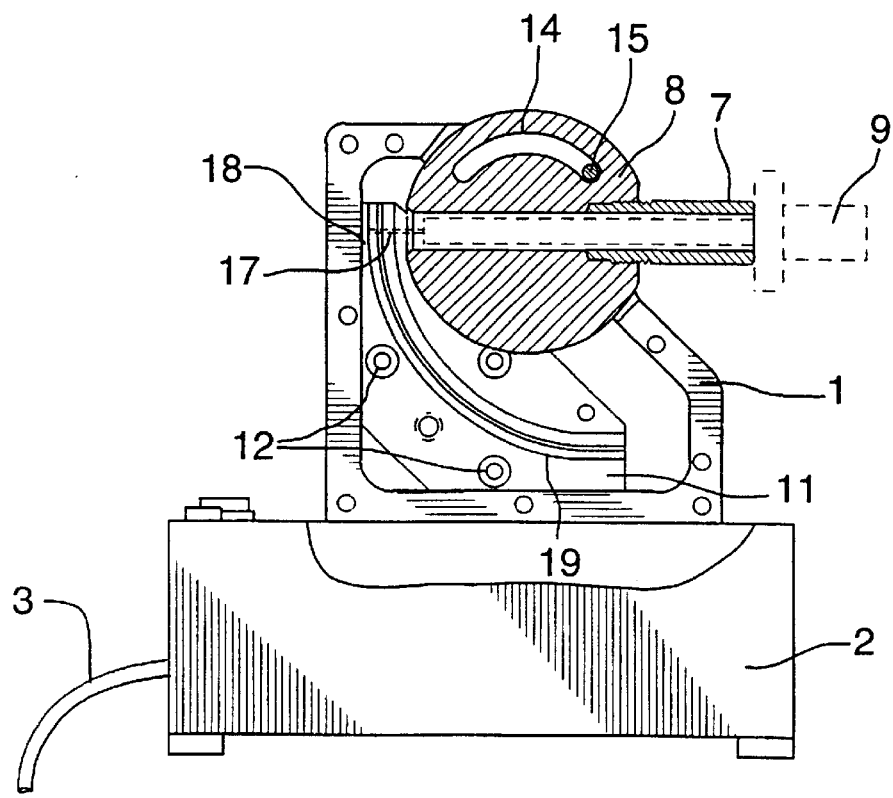
FIG. 5 is a sectional elevation view along line 5—5 of FIG. 3, with the holder in an lower finish position, wherein the metal needle shank has been progressively burned advancing the burning tip to the hilt of the metal needle.

A removable mandrel 7 is removably attached to a rotating turret 8. As best seen in FIGS. 3, 4 and 5, the mandrel 7 is configured to mate with the medical instrument 9, which in the example of the drawings is a hypodermic needle 9. It will be understood that the mandrel 7 can be made in various configurations to match the size and shape of instruments to be destroyed. In the case of hypodermic needles 9, three or four adapter mandrels 7 that have threaded ends engaging a threaded hole in the turret 8 are expected to be able to accommodate the bulk of commonly used needles 9.

The turret 8 and removable mandrel 7 therefore provide a means to position or locate the needle 9 and to hold the instrument 9 during the destruction process. Medical instruments 9 which may be adapted to utilise the invention include hypodermic needles, syringes, scalpels, sutures and other metallic cutting means, all of which have a sharp tip and elongate shaft with a longitudinal axis. As illustrated in FIGS. 3, 4 and 5, first and second electrodes 10 and 11 are secured statically within the housing with bolts 12. Preferably the electrodes 10 and 11 are of copper, which may be coated to extend their serviceable life with beryllium, beryllium oxide, gold, titanium or other commonly used conductive coatings.

FIG. 3 best shows the turret 8 being journalled on trunions 13 in the housing 1 for rotation about a transverse (horizontal) axis. The extent of rotation, in FIGS. 4 and 5, is limited to 90 degrees with the use of an sliding circular arc 14 (within the turret 8) and stationary pin 15 mechanism.

FIG. 3 shows that the electrodes 10 and 11 each have tapered electrical contact surfaces disposed in opposition and separated by a gap 16. The tapered contact surfaces taper 19 outwardly from the longitudinal axis of the instrument 9 to accommodate varying sizes of metallic portions of various instruments. For example, commonly used diabetic, or similar hypodermic needles 9 of varying width directed at the gap 16 can electrically contact both tapered surfaces easily without requiring modification of the electrode 10 and 11 spacing or configuration.

Briefly stated, the electrodes 10 and 11, as shown in FIGS. 4 and 5, have a concave electrical contact surface 19 to provide a progressive advancement of the burning of the tip 18 of the instrument 9. As the turret 8 is rotated between the positions shown in FIG. 4 to that of FIG. 5, the burning tip 18 progressively consumes the shaft 17 of the instrument 9 continuously in contact with the electrodes 10 and 11.

The method of utilising the device to destroy the metallic needle portion of an elongate hypodermic syringe 9 is as follows. With reference to FIG. 4, the syringe 9 is manually slid or moved to the start position shown wherein the tip 18 of the needle 9 engages the contact surface 19 of each electrode 10 and 11.

The tip 18 of the metallic needle portion of the syringe makes electrical contact with the contact surfaces 19 of both electrodes 10 and 11 thereby spanning the gap 16 and completing an electrical circuit. Each electrode is in contact with the electrical power source. The power source creates an electrical potential difference between the electrodes 10 and 11 which is sufficient to induce electrical resistance burning of the tip 18 of the instrument 9 when the electrical current is passed through the tip 18 between electrodes 10 and 11.

Due to the exceedingly thin tube of stainless steel of which needles 9 are made, it has been found that very low levels of electrical power are required to induce such resistance burning. Needles 9 are made of stainless steel, which have a melting point in the range of 2600 to 2800 degrees Fahrenheit, impede electrical conductance creating heat. The thin walls of the tip 18 provide a direct path for the electric circuit between electrodes 10 and 11. Localised high heat results in the at the tip 18 in the range of 2400 to 2800 degrees Fahrenheit. This range of heat is above the melting point of the needle 9 metal which burns the tip 18 quickly.

In addition, the high heat at the tip 18 is conducted via the metal shaft 17 to the remaining portions of the hypodermic syringe. It has been found that heat in the range of 1400 to 1600 degrees Fahrenheit (750 to 875 degrees Celsius) results in the remaining portions of the instrument 9 above the burned metal portion. This heat sterilises the remaining stub portions of the hypodermic syringe, further reducing risk of contamination.

If the instrument 9 were to remain stationary, the tip 18 would briefly contact the electrodes 10 and 11 and burn or melt away enough metal until electrical contact ceased.

Therefore to maintain continuous electrical contact and progressively burn the shaft 17 of the needle 9, the rotating turret 8 provides means to progressively advance the instrument 9 and the electrodes 10 and 11 longitudinally relative to each other. As a result, the burning of the tip 18, as the turret 8 is rotated, consumes the shaft 17 as the burning tip 18 advances from the start position (shown in FIG. 4) to the finish position (shown in FIG. 5) continuously in electrical contact with each electrode 10 and 11.

The progressive burning of the tip 18 may be accomplished by many mechanical advancing means, however the drawings show a simple cam construction to illustrate the principle. The concave contact surfaces 19 of each electrode 10 and 11 are shown as of constant radius R forming a circular arc centred about a contact surface centre. To advance the tip 18 longitudinally relative to the electrodes 10 and 11, the transverse axis about which the turret 8 rotates is eccentric or inwardly displaced relative to the contact surface centre. This simple construction using circular surfaces and rotation may be easily constructed using conventional machine tools. More complex cam shapes such as parabolic, spiral etc. may of course also be used but the machining setup is more complex as well.

Figure 8:
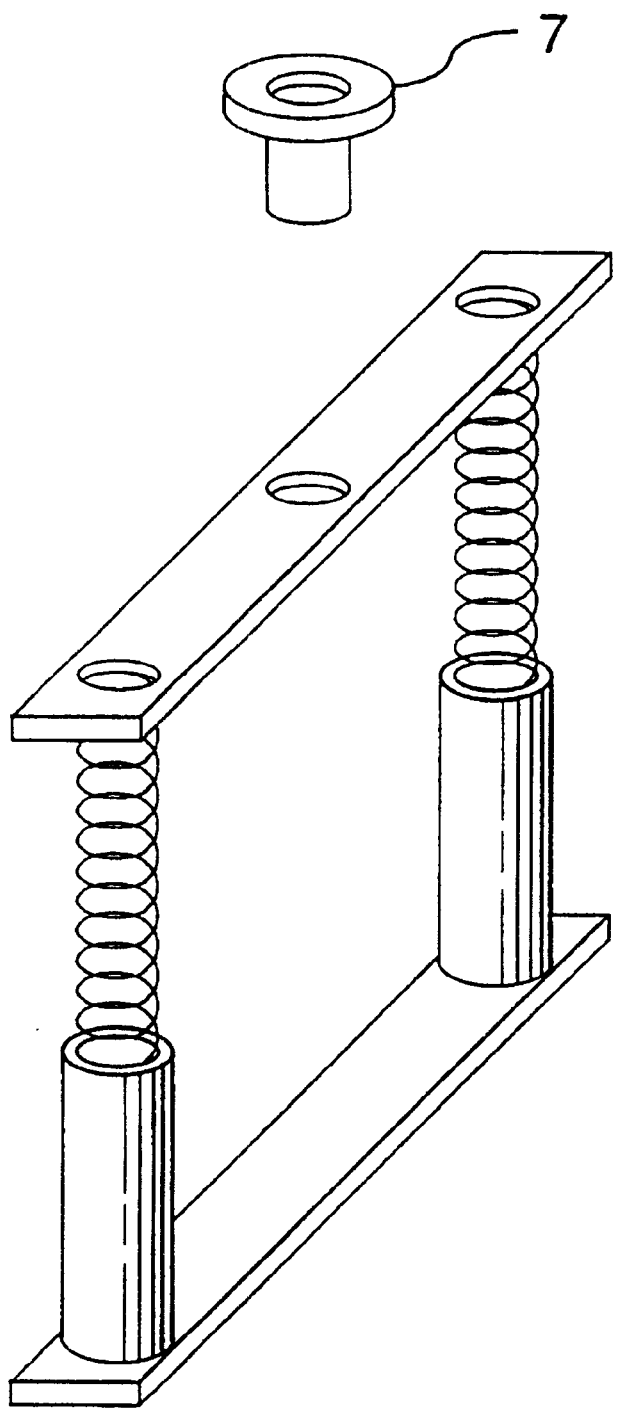
FIG. 8 is an exploded detail view of an alternative means for advancing the instrument towards the rotating electrodes using a spring loaded telescoping guide.

Advantageously, the mandrel 7 may include a spring loaded collar mechanism as shown in FIG. 8, a counterweighted collar or other common means to position the instrument 9 in a standby position similar to that shown in FIG. 4. The standby position is defined as where the tip 18 of the instrument 9 is disengaged from the contact surface 19 of each electrode 10 and 11. The accidental commencement of burning can thus be prevented, and where the power is left on continuously, the user can clearly control commencement of burning by pushing the instrument 9 down from the standby position to a start position.

Figure 6:
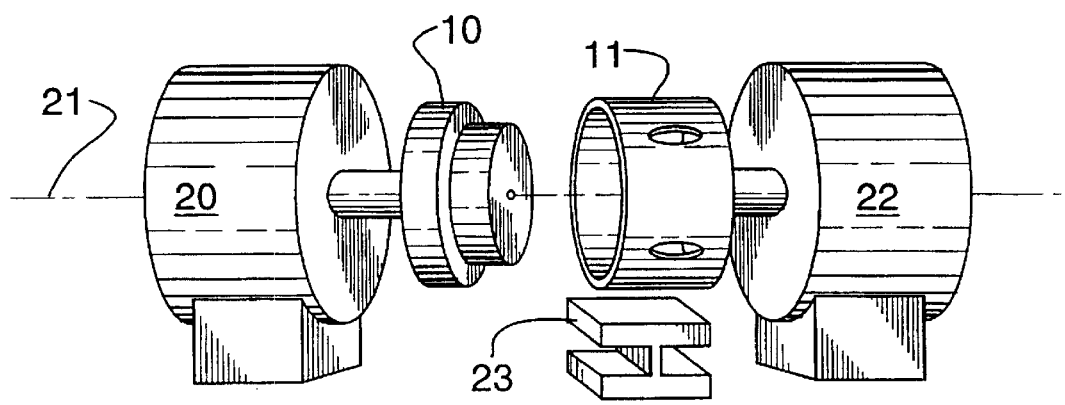
FIG. 6 is a partially exploded perspective view of a second embodiment of a device wherein the electrodes are a disk to the left and a mating drum to the right, which are rotated counter to each other by the electric motors to which they are mounted.
Figure 7:
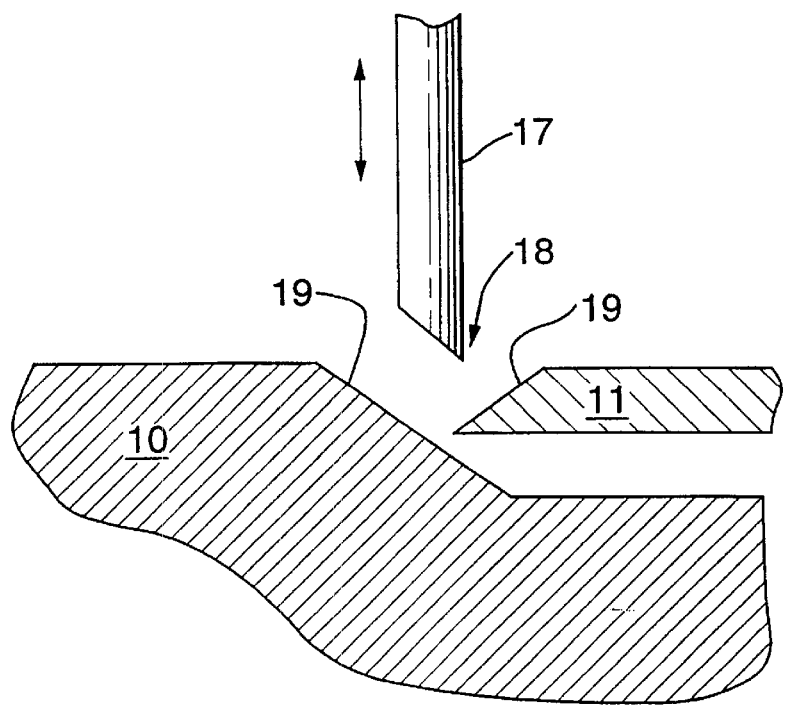
FIG. 7 is a detail view of the disposition of a needle point tip into the gap between the assembled electrodes of FIG. 6.

FIGS. 6 and 7 show a second preferred embodiment of the invention. In this example, the electrodes 10 and 11 are configured as counter-rotating, whereas the tip 18 of instrument is slid radially into contact with the tapered electrical contact surfaces 19.

The primary advantages of counter-rotating electrodes are a self cleaning function, speed of metal consumption, and ease of operation.

Although it is possible to achieve some of these advantages using a single rotating first electrode 10, driven by a first electric motor 20 about an electrode axis 21, it is considered preferable to provide a second electric motor 22 to rotate the second electrode 11 about the same axis 21 in a counter direction relative to the first electrode 11.

By utilising two counter, rotating electrodes 10 and 11, metallic debris from the burning process does not build up between the electrodes 10 and 11. The centrifugal force of rotation drives the debris radially outwardly where it may be collected on a magnet 23. Repairs, cleaning and dressing of damaged contact surfaces 19 can be easily accomplished by mounting the electrodes 10 and 11 on a lathe.

As illustrated, the electrodes 10 and 11 may comprise a disc and drum respectively where the first electrode 10 is disposed partially within the second drum electrode 11. FIG. 7 shows the advantage of using a disk 10 and drum 11 arrangement since debris between the electrodes may be expelled through perforations 24 in the second electrode 11.

Although the above description and accompanying drawings relate to a specific preferred embodiment as presently contemplated by the inventor, it will be understood that the invention in its broad aspect includes mechanical and functional equivalents of the elements described and illustrated.

I claim:

1. A device for destroying a metallic portion of an elongate medical instrument having a longitudinal axis, a tip and shaft, the device comprising:

a housing;

first and second electrodes in the housing, each electrode having an electrical contact surface disposed in opposition and separated by a gap;

means for moving the instrument to a start position wherein the tip of the instrument electrically engages the contact surface of each electrode;

power source means for creating an electrical potential difference between the electrodes, the potential difference being sufficient to induce electrical resistance burning of the tip of the instrument when an electrical current is passed through the tip between the electrodes; and advancing means for progressively advancing the instrument and the electrodes longitudinally relative to each other, whereby the burning of the tip of the instrument progressively consumes the shaft as the burning tip advances from the start position to a finish position continuously in electrical contact with each electrode.

2. A device according to claim 1 including positioning means for positioning the instrument in a standby position, wherein the tip of the instrument is disengaged from the contact surface of each electrode.

3. A device according to claim 1, wherein the contact surface of each electrode is tapered outwardly from the longitudinal axis of the instrument.

4. A device according to claim 1, wherein the electrodes have a concave contact surface and are statically housed in the housing, and wherein the advancing means comprise an instrument holder journalled in the housing about a transverse axis.

5. A device according to claim 4, wherein the concave surface has a constant radius about a contact surface centre and the transverse axis is eccentric said centre.

6. A device according to claim 1, comprising means for rotating the first electrode about an electrode axis.

7. A device according to claim 6, comprising means for counter rotating the second electrode relative to the first electrode and about the electrode axis.

8. A device according to claim 7, wherein the first and second electrodes comprise a disc and drum respectively.

9. A device according to claim 8, wherein the contact surface of each electrode is tapered outwardly from the longitudinal axis of the instrument.

10. A device according to claim 8, wherein the advancing means comprise a spring loaded collar.

11. A device according to claim 8, wherein the advancing means comprise a counterweighted collar.

12. A device according to claim 8, wherein the first electrode is disposed partially within the second electrode.

13. A device according to claim 12, wherein the second electrode is perforated.

14. A device according to claim 13, including magnetic collector means for collecting metallic debris resulting from the burning of the metallic instrument.

15. A device according to claim 1, wherein the positioning means include a removable mandrel configured to mate with the instrument.

16. A device according to claim 1, comprising at least one copper electrode.

17. A device according to claim 16, wherein the copper electrode is coated with a substance selected from the group consisting of: beryllium; beryllium oxide; gold; and titanium.

18. A device according to claim 1, wherein the power source means are selected from the group consisting of: a transformer; a battery; a mobile power source.

19. A device according to claim 18, wherein the transformer converts 110 volt intake to output in the range of 3.15 to 12 volts.

20. A method of destroying a metallic portion of an elongate medical instrument having a longitudinal axis, a tip and shaft, the method comprising the steps of:

locating the instrument in a position wherein the tip of the instrument electrically engages a contact surface of a first and second electrode, each electrode having said electrical contact surface disposed in opposition and separated by a gap, and each electrode in electrical contact with power source means for creating an electrical potential difference between the electrodes, the potential difference being sufficient to induce electrical resistance burning of the tip of the instrument when an electrical current is passed through the tip between the electrodes; and progressively advancing the instrument and the electrodes longitudinally relative to each other, whereby the burning of the tip of the instrument progressively consumes the shaft as the burning tip advances from the start position to a finish position continuously in electrical contact with each electrode.

* * * * *

UNITED STATES PATENT AND TRADEMARK OFFICE
CERTIFICATE OF CORRECTION

PATENT NO. : 6,337,454 B1
DATED : January 8, 2002
INVENTOR(S) : Walker

It is certified that error appears in the above-identified patent and that said Letters Patent is hereby corrected as shown below:

Title page,
Item [73], Assignee, remove "Jack Warbold, St Catharines, (CA.)" and add
-- Progressive Management Group, Inc. --

Signed and Sealed this

Twenty-second Day of March, 2005

JON W. DUDAS
*Director of the United States Patent and Trademark Office*